(12) United States Patent
Ravindran et al.

(10) Patent No.: US 10,376,243 B2
(45) Date of Patent: Aug. 13, 2019

(54) METHOD AND APPARATUS FOR LOW COMPLEXITY ULTRASOUND BASED HEART RATE DETECTION

(71) Applicant: Texas Instruments Incorporated, Dallas, TX (US)

(72) Inventors: Sourabh Ravindran, Dallas, TX (US); Jonathon David Spaulding, Mountain View, CA (US)

(73) Assignee: Texas Instruments Incorporated, Dallas, TX (US)

( * ) Notice: Subject to any disclaimer, the term of this patent is extended or adjusted under 35 U.S.C. 154(b) by 633 days.

(21) Appl. No.: 14/497,295

(22) Filed: Sep. 25, 2014

(65) Prior Publication Data

US 2015/0094592 A1    Apr. 2, 2015

Related U.S. Application Data

(60) Provisional application No. 61/883,563, filed on Sep. 27, 2013.

(51) Int. Cl.
| | | |
|---|---|---|
| *A61B 8/00* | (2006.01) | |
| *A61B 8/02* | (2006.01) | |
| *A61B 8/08* | (2006.01) | |

(52) U.S. Cl.
CPC ............ *A61B 8/5223* (2013.01); *A61B 8/02* (2013.01); *A61B 8/488* (2013.01); *A61B 8/5207* (2013.01); *A61B 8/462* (2013.01)

(58) Field of Classification Search
CPC .................................................... A61B 8/02
See application file for complete search history.

(56) References Cited

U.S. PATENT DOCUMENTS

| | | | | |
|---|---|---|---|---|
| 4,299,234 A | * | 11/1981 | Epstein | A61B 5/02411 600/511 |
| 5,175,709 A | * | 12/1992 | Slayton | B06B 1/0629 310/326 |
| 5,183,040 A | * | 2/1993 | Nappholz | A61B 8/06 600/439 |
| 5,653,234 A | * | 8/1997 | Kim | G01S 7/52077 382/264 |
| 5,724,032 A | * | 3/1998 | Klein | A61B 5/024 341/50 |
| 6,192,090 B1 | * | 2/2001 | Lee | H04L 1/20 375/278 |

(Continued)

*Primary Examiner* — Tse W Chen
*Assistant Examiner* — Jason M Ip
(74) *Attorney, Agent, or Firm* — Ebby Abraham; Charles A. Brill; Frank D. Cimino

(57) ABSTRACT

A method for ultrasound based heart rate detection in a heart rate monitoring system is provided that includes receiving a demodulated Doppler ultrasound signal, applying a band-pass filter to the demodulated Doppler ultrasound signal to remove a direct current (DC) component and out-of-band noise, wherein a filtered demodulated Doppler ultrasound signal is generated, rectifying the filtered demodulated Doppler ultrasound signal to generate a rectified filtered demodulated Doppler ultrasound signal, applying a low-pass filter to the rectified filtered demodulated Doppler ultrasound signal to filter out undesired components to leave a resulting signal corresponding to power shift due to heart rate, detecting peaks in the resulting signal, and computing a heart rate based on the detected peaks.

10 Claims, 4 Drawing Sheets

(56) References Cited

U.S. PATENT DOCUMENTS

| | | | |
|---|---|---|---|
| 6,599,248 B1* | 7/2003 | Tamura | A61B 8/06 600/454 |
| 2003/0011473 A1* | 1/2003 | Progovac | G08B 13/181 340/552 |
| 2007/0263842 A1* | 11/2007 | Pessoa | H04Q 1/44 379/283 |
| 2008/0076374 A1* | 3/2008 | Grenader | H04B 1/1027 455/307 |
| 2012/0313809 A1* | 12/2012 | Testar | G01S 7/292 342/118 |
| 2013/0033203 A1* | 2/2013 | Luke | B60L 1/003 318/376 |
| 2013/0123637 A1* | 5/2013 | Wohlschlager | A61B 8/02 600/453 |
| 2013/0245478 A1* | 9/2013 | Zhang | A61B 5/0402 600/521 |

\* cited by examiner

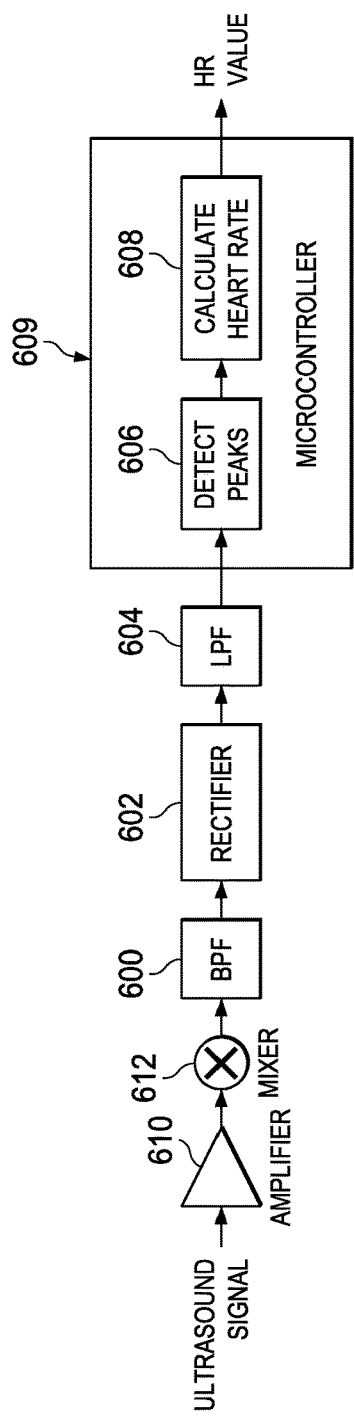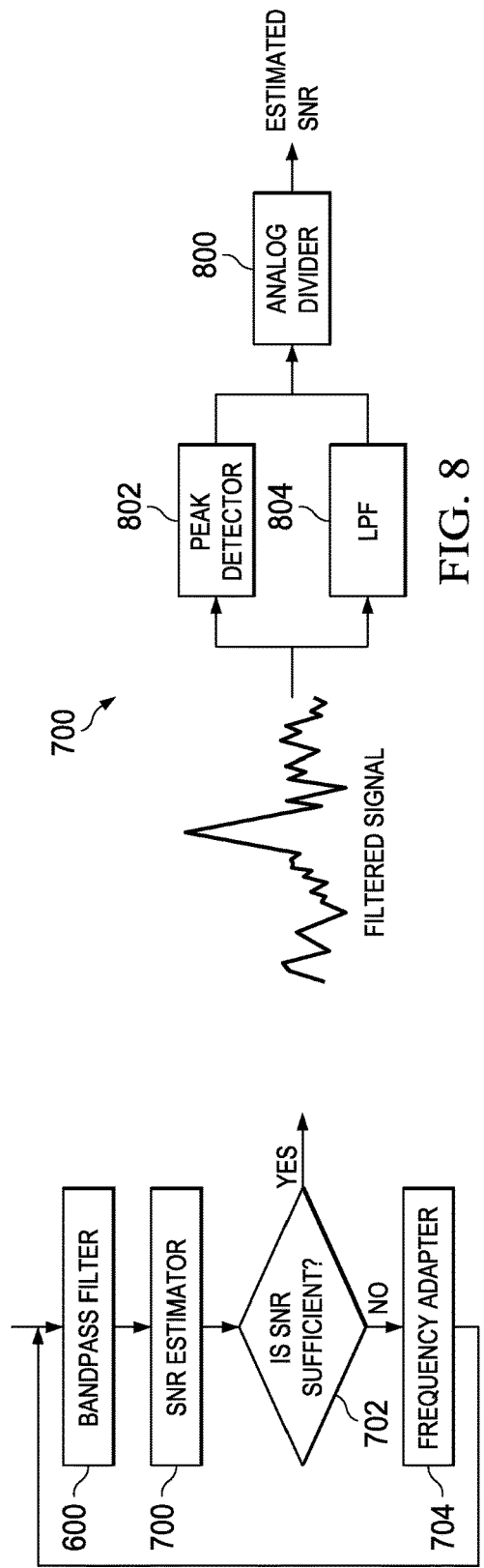

METHOD AND APPARATUS FOR LOW COMPLEXITY ULTRASOUND BASED HEART RATE DETECTION

CROSS-REFERENCE TO RELATED APPLICATIONS

This application claims benefit of U.S. Provisional Patent Application Ser. No. 61/883,563, filed Sep. 27, 2013, which is incorporated by reference herein in its entirety.

BACKGROUND OF THE INVENTION

Field of the Invention

Embodiments of the present invention generally relate to ultrasound based heart rate detection.

Description of the Related Art

Doppler ultrasound is a commonly used imaging modality for the medical monitoring of a patient. In this modality, either pulsed or continuous wave ultrasound signals are targeted at a blood vessel of a patient. The reflected pressure waves exhibit a Doppler shift which is dependent upon the transmission frequency, the angle of insonification of the probe, and the velocity of the targeted blood. This velocity information carries physiological information which can be used to diagnose varying conditions such as obstructions or reverse blood flow. Varying post-processing techniques exist in the frequency domain to isolate the signal characteristics of interest.

SUMMARY

Embodiments of the present invention relate to methods, apparatus, and computer readable media for ultrasound based heart rate detection. In one aspect, a method for ultrasound based heart rate detection in a heart rate monitoring system is provided that includes receiving a demodulated Doppler ultrasound signal, applying a bandpass filter to the demodulated Doppler ultrasound signal to remove a direct current (DC) component and out-of-band noise, wherein a filtered demodulated Doppler ultrasound signal is generated, rectifying the filtered demodulated Doppler ultrasound signal to generate a rectified filtered demodulated Doppler ultrasound signal, applying a low-pass filter to the rectified filtered demodulated Doppler ultrasound signal to filter out undesired components to leave a resulting signal corresponding to power shift due to heart rate, detecting peaks in the resulting signal, and computing a heart rate based on the detected peaks.

In one aspect, a heart rate monitoring system is provided that includes circuitry for applying a bandpass filter to a demodulated Doppler ultrasound signal to remove a direct current (DC) component and out-of-band noise, wherein a filtered demodulated Doppler ultrasound signal is generated, circuitry for rectifying the filtered demodulated Doppler ultrasound signal to generate a rectified filtered demodulated Doppler ultrasound signal, circuitry for applying a low-pass filter to the rectified filtered demodulated Doppler ultrasound signal to filter out undesired components to leave a resulting signal corresponding to power shift due to heart rate, means for detecting peaks in the resulting signal, and means for computing a heart rate based on the detected peaks.

BRIEF DESCRIPTION OF THE DRAWINGS

Particular embodiments will now be described, by way of example only, and with reference to the accompanying drawings:

FIGS. 6, 7, and 8 are block diagrams illustrating aspects of exemplary Doppler ultrasound based heart rate detection devices.

DETAILED DESCRIPTION OF EMBODIMENTS OF THE INVENTION

Figure 1:
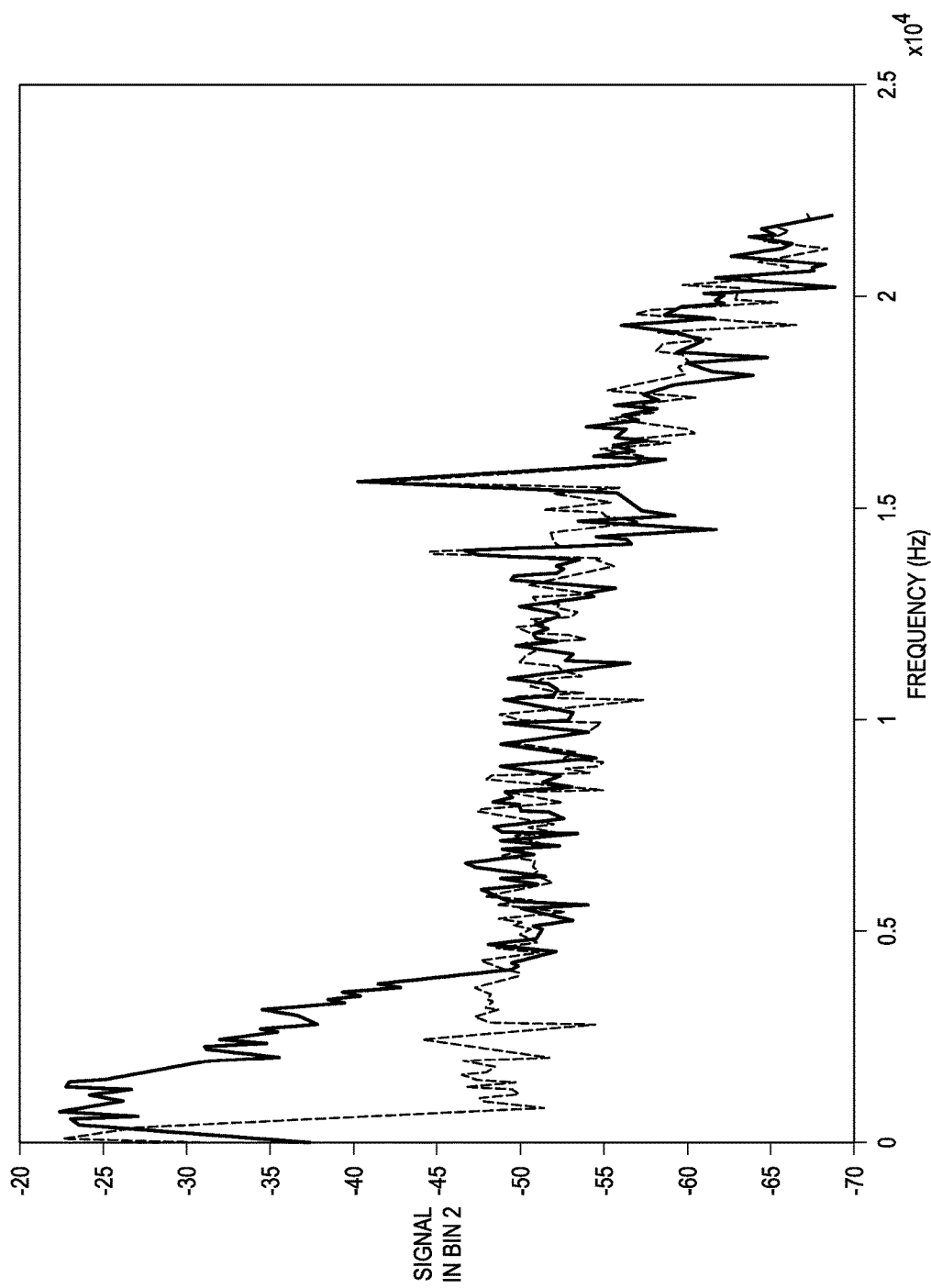
FIG. 1 is a graph contrasting the power spectrum of a Doppler ultrasound signal during systolic and diastolic phases.

Specific embodiments of the invention will now be described in detail with reference to the accompanying figures. Like elements in the various figures are denoted by like reference numerals for consistency.

Embodiments of the invention provide for heart rate detection based on detecting the power shift in Doppler ultrasound signals due to time-varying flow velocity changes in a blood vessel. An examination of the signal properties of a Doppler ultrasound signal in a heart rate monitoring system shows that the signal FFT is characterized by a periodic shift of spectral power. During the systolic phase of the heart beat, blood is travelling quickly, and the system exhibits more power at higher frequency shifts from the carrier. During the diastolic phase, blood travels much slower, resulting in power being centralized at lower frequency shifts. This is common knowledge observed from looking at a standard spectrogram of the data. An example measurement contrasting the power spectrum of the signal during the systolic and diastolic phases is shown in FIG. 1.

A prior approach to processing a Doppler ultrasound signal for heart rate detection amplifies the signal with a low-noise amplifier (LNA), demodulates the amplified signal with the transmit frequency, and passes the resulting signal through a severe high-pass filter to attenuate any large dynamic range, low frequency shift artifacts. Often, both the I (in phase) and Q (quadature phase) components of the demodulator are used to track the full frequency content of the signal.

In some embodiments of the invention, only the I channel is used, which lends itself to less hardware (and thus lower power consumption) in the signal processing path. In embodiments of the invention, the high-pass filter of the prior art is replaced with a bandpass filter. The bandpass filter has the same effect of reducing low-frequency artifacts, and additionally limits the amount of out-of-band noise present in the system. Overall system performance is not affected as frequency shift information is necessarily constrained to a particular frequency band dependent upon the blood velocity and transducer angle to the target. Once the signal has been processed with the bandpass filter, the signal is rectified using, for example, an active full-wave rectifier. This has the effect of altering the frequency profile of the signal. For a signal with no direct current (DC) components, this has the effect of doubling undesired frequencies, which when passed through a low-pass filter, are further attenuated. By setting the passband of a following low-pass filter to the highest expected frequency for a heart rate (e.g., 4 Hz), the undesired components of the signal are filtered out to leave the signal corresponding to the spectral power shift due to the heart rate behind. Peak detection is then performed on the smoothed signal to detect peaks which are used for heart rate calculation.

Embodiments may be based on a fully analog time-domain approach as opposed to the digital signal processor (DSP) intensive frequency domain or autocorrelation techniques commonly used. Some embodiments may be implemented entirely in analog circuitry, thereby reducing the overall system power consumption and lending the topology to a fully integrated analog front end integrated circuit.

Figure 2:
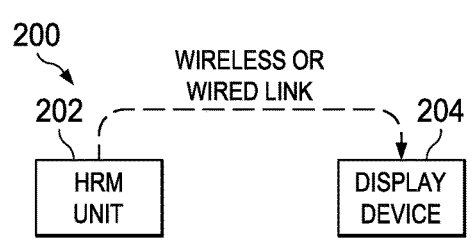
FIGS. 2 and 3 are block diagrams of exemplary heart rate monitoring systems.
Figure 3:
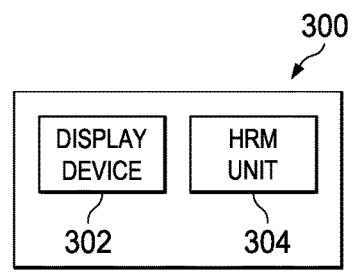
Figure 4:
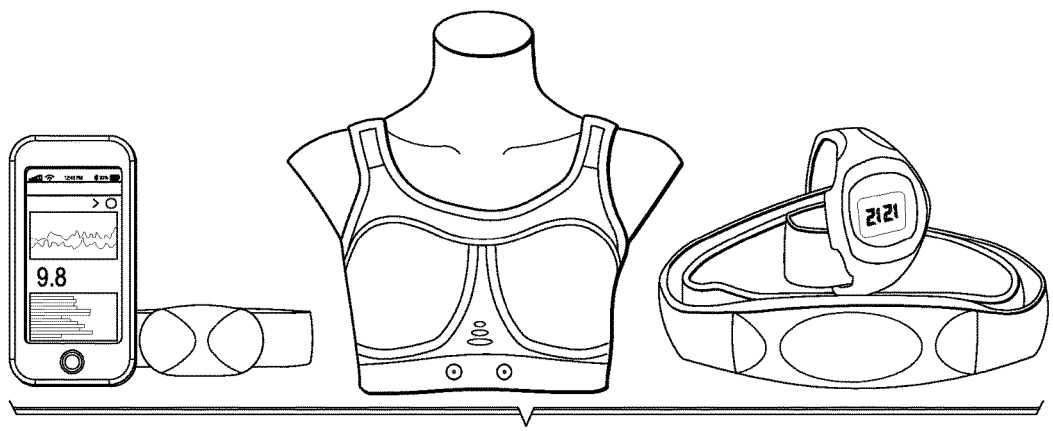
FIGS. 4 and 5 are example form factors of heart rate monitoring systems.

FIGS. 2 and 3 are block diagrams of exemplary heart rate monitoring systems incorporating a heart rate monitor (HRM) unit implementing the Doppler ultrasound based heart rate detection described herein. In some embodiments, the HRM unit is an analog circuit implementing the heart rate detection described herein. In FIG. 2, the heart rate monitoring system 200 includes an HRM unit 202 and a display device 204 that communicate via a wired or wireless communication link. More specifically, the HRM unit 202 and the display device 204 are not implemented as a single device in the same housing. Some embodiments may allow for the asymmetric splitting of power between sensor and heart rate detector to enable new device form factors. The HRM unit 202 may be incorporated in form factors with no display capability such as, for example, a chest strap, a wrist strap (e.g., a watch-like form factor), an arm band, a sports bra, or a finger mount. FIG. 4 shows some example form factors for housing the HRM unit 202. The display device 202 may be any suitable display device, such as, for example, a smart phone, a display on a medical monitoring device, a display on exercise equipment such as a treadmill or an elliptical machine, or a display on a watch. The HRM unit 202 computes the heart rate of the person having the unit somehow mounted on his or her body and communicates that heart rate to the display device 202 over the wireless or wired link.

Figure 5:
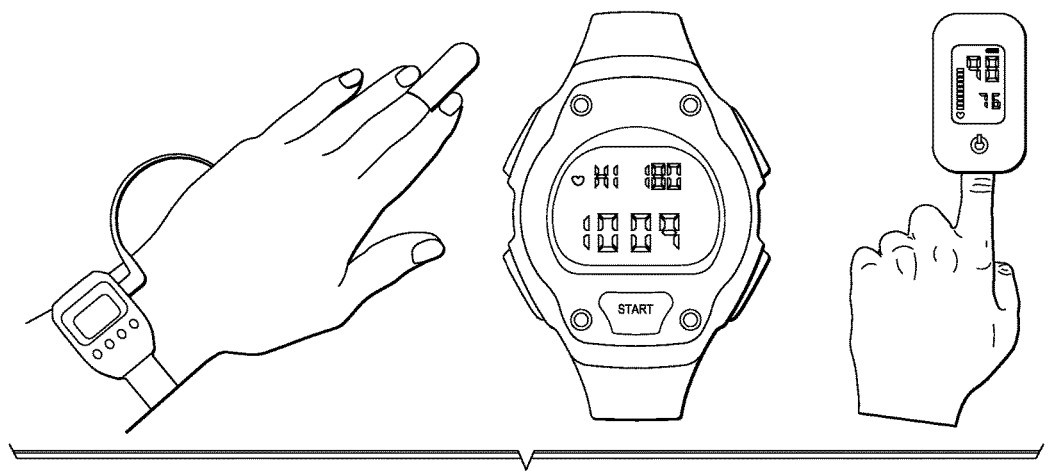

In FIG. 3, the heart rate monitoring system includes a HRM unit 304 and a display device 302 in a common housing. For example, the HRM unit 304 and the display device 302 may be combined in a wrist mounted device (e.g., a watch-like form factor) or a finger mounted device. FIG. 5 shows some example form factors for housing both the HRM unit 304 and the display device 302. The HRM unit 304 computes the heart rate of the person having the unit somehow mounted on his or her body and communicates that heart rate to the display device 302 for display.

FIG. 6 shows a block diagram of an example Doppler ultrasound based heart rate detection device that may be implemented in an HRM unit such as that of FIGS. 1 and 2. The system includes band pass filter circuitry 600, rectifier circuitry 602, low-pass filter circuitry 604, a microcontroller 609, an amplifier 610, and a mixer 612. The device accepts as input a Doppler ultrasound signal, e.g., from an ultrasound transducer, and outputs a calculated heart rate. The Doppler ultrasound signal may be, for example, a pulsed wave Doppler ultrasound signal, a continuous wave Doppler ultrasound signal, or any other suitable Doppler ultrasound signal.

The amplifier 610 operates to amplify the received ultrasound signal and the mixer 612 operates to demodulate the amplified signal. The mixer may be implemented in either a passive or active topology, and the mixing signal may or may not include harmonic rejection. The bandpass filter circuitry 600 operates to remove the DC component of the signal and to remove out-of-band noise from the demodulated signal. The rectifier circuitry 602 implements an active full-wave rectifier or an active half-wave rectifier that alters the frequency profile of the signal and in conjunction with the low-pass filter acts as a peak detector.

The low-pass filter circuitry 604 operates to filter out the undesired components of the rectified signal, leaving the signal corresponding to frequency shift related to heart rate. The passband of the low-pass filter may be set to a frequency that will filter out frequencies that are too high to correspond to a heart rate. For example, the passband frequency may be the highest expected frequency for a heart rate, e.g., 4 Hz.

The microcontroller 609 is programmed to receive the filtered signal from the low-pass filter circuitry 604, to detect peaks 606 in the filtered signal, and to calculate 608 the heart rate based on the detected peaks. Calculation of heart rate from detected signal peaks is well-known and any suitable calculation technique may be used. In some embodiments, rather than having the microcontroller 609 include peak detection, the peak detection may be analog circuitry.

There may be large ultrasound signal variability from person to person. Specifically, both the blood velocity variation as well as the placement of the ultrasound transducer may result in different signal power spectrums among individuals. As such, a single fixed-frequency bandpass filter may not yield the best results. In practice, it may be desirable to adjust the lower corner of the bandpass filter to compensate for this variation. Thus, in some embodiments, a dynamic feedback loop is incorporated in the heart rate detection device of FIG. 6 to calibrate the lower cutoff frequency of the bandpass filter based on the signal integrity. This dynamic feedback loop may be used for initial calibration of the device and for periodic re-calibration to adapt for any movement of the ultrasound transducer.

FIGS. 7 and 8 are block diagrams showing example circuitry for such a feedback loop. As shown in FIG. 7, the lower corner (lower cutoff frequency) of the bandpass filter 600 is iteratively adapted until a sufficient signal to noise (SNR) ratio is achieved 702. In some embodiments, a pre-determined SNR threshold may be used, e.g., an SNR threshold of approximately 10 dB or higher. In some embodiments, the feedback loop may adaptively determine what the sufficient SNR is. SNR estimator circuitry 700 operates to estimate the SNR of a peak in the signal and the "average" signal. Frequency adaptor circuitry 704 operates to modify the lower cutoff frequency of the bandpass filter 600 until the SNR is sufficient.

FIG. 8 is a block diagram of example SNR estimation circuitry 700. The peak detector circuitry 802 operates to find the peak of the signal (as filtered by the bandpass filter 600 with the current lower cutoff frequency) and the low-pass filter circuitry 804 operates to determine the "average" signal from the input signal. The analog divider circuitry 800 operates to divide the peak by the average to estimate the SNR.

One implementation of this feedback loop is to incorporate a capacitor bank with switches in the device to control the lower frequency corner of the bandpass filter. During an initial calibration phase or during a periodic re-calibration phase, the device can sequentially switch these capacitors in and out, effectively monitoring the device output as the filter corner is changed. The SNR between the signal peak and the average signal for each filter setting can be used to determine a customized filter setting which yields better quality heart rate date for a particular individual.

Figure 9:
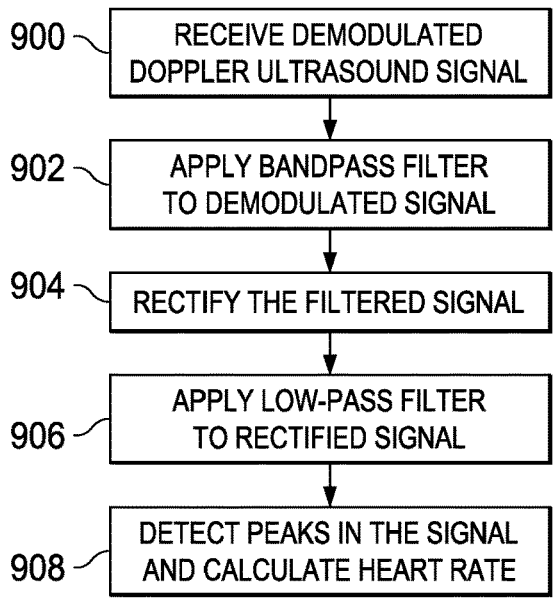
FIGS. 9 and 10 are flow diagrams of methods for Doppler ultrasound based heart rate detection.
Figure 10:
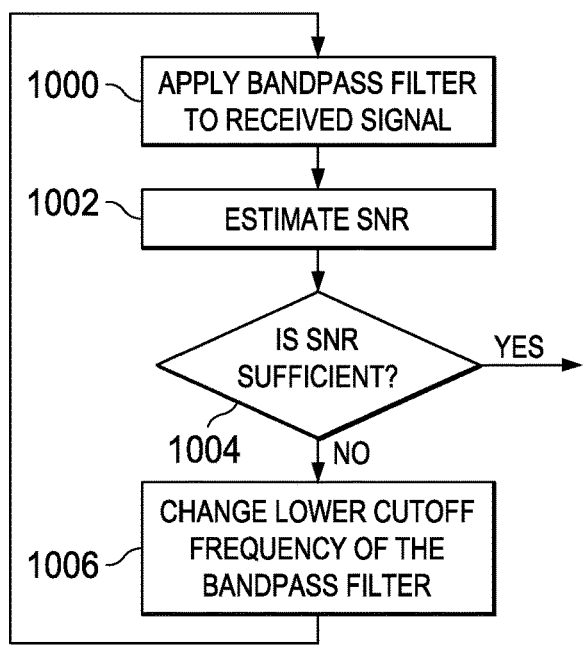

FIGS. 9 and 10 are flow diagrams of methods for Doppler ultrasound based heart rate detection in a heart rate monitoring system. FIG. 9 is a flow diagram of a basic method for heart rate detection using Doppler ultrasound and FIG. 10 is a flow diagram of a method for calibrating the method of FIG. 9 to a person using the heart rate monitoring system.

Referring first to FIG. 9, initially a demodulated Doppler ultrasound signal is received 900 from an ultrasound source, e.g., an ultrasound transducer, deployed on the body of a person using the heart rate monitoring system. In some embodiments, the demodulated signal is the I channel of the ultrasound signal. A bandpass filter is applied 902 to the demodulated signal to remove the DC component of the signal and the out-of-band noise. The filtered signal is then rectified 904 using, for example, active full-wave rectification or active half-wave rectification. A low-pass filter is then applied 906 to the rectified signal to filter out the undesired components and leave the signal corresponding to frequency shift related to heart rate. The passband of the low-pass filter may be set to the highest frequency expected for a heart rate, e.g., 4 Hz. Peaks are then detected 908 in the resulting signal and the heart rate is calculated based on the detected peaks.

As previously mentioned, there may be large ultrasound signal variability from person to person, so it is may be desirable to compensate for this variation. A dynamic feedback loop may be incorporated into the method of FIG. 9 to calibrate the method for the person using the heart rate monitoring system. This dynamic feedback loop may be used for initial calibration of the device and for periodic re-calibration to adapt for any movement of the ultrasound source.

FIG. 10 is a flow diagram of a method for calibration that may be incorporated in the method of FIG. 9. As shown in FIG. 10, the bandpass filter is applied 1000 to the received demodulated Doppler ultrasound signal. The SNR is then estimated 1002. Estimation of SNR is previously described herein. If the SNR is not sufficient 1004, then the lower cutoff frequency of the band pass filter is changed 1006 and the process is repeated. When the SNR is sufficient 1004, the calibration process is terminated.

Other Embodiments

While the invention has been described with respect to a limited number of embodiments, those skilled in the art, having benefit of this disclosure, will appreciate that other embodiments can be devised which do not depart from the scope of the invention as disclosed herein.

The methods described herein may be implemented in hardware, software, firmware, or any combination thereof. If completely or partially implemented in software, the software may be executed in one or more processors, such as a microcontroller, microprocessor, application specific integrated circuit (ASIC), field programmable gate array (FPGA), or digital signal processor (DSP). The software instructions may be initially stored in a computer-readable medium and loaded and executed in the processor. In some cases, the software instructions may also be sold in a computer program product, which includes the computer-readable medium and packaging materials for the computer-readable medium. In some cases, the software instructions may be distributed via removable computer readable media, via a transmission path from computer readable media on another digital system, etc. Examples of computer-readable media include non-writable storage media such as read-only memory devices, writable storage media such as disks, flash memory, memory, or a combination thereof.

Although method steps may be presented and described herein in a sequential fashion, one or more of the steps shown in the figures and described herein may be performed concurrently, may be combined, and/or may be performed in a different order than the order shown in the figures and/or described herein. Accordingly, embodiments should not be considered limited to the specific ordering of steps shown in the figures and/or described herein.

It is therefore contemplated that the appended claims will cover any such modifications of the embodiments as fall within the true scope of the invention.

What is claimed is:

1. A method comprising:
   receiving a demodulated Doppler ultrasound signal;
   applying a bandpass filter to the demodulated Doppler ultrasound signal to generate a filtered demodulated Doppler ultrasound signal;
   determining a peak in the filtered demodulated Doppler ultrasound signal;
   determining, using a first low-pass filter, an average of the filtered demodulated Doppler ultrasound signal;
   estimating a signal-to-noise ratio (SNR) based on the peak and average of the filtered demodulated Doppler ultrasound signal;
   modifying a lower cutoff frequency of the bandpass filter based on the estimated SNR when the estimated SNR is below a pre-determined SNR threshold;
   applying the modified bandpass filter to the filtered demodulated Doppler ultrasound signal to generate a double-filtered demodulated Doppler ultrasound signal;
   rectifying the double-filtered demodulated Doppler ultrasound signal to generate a rectified filtered demodulated Doppler ultrasound signal;
   applying a second low-pass filter to the rectified filtered demodulated Doppler ultrasound signal to generate a resulting signal;
   detecting peaks in the resulting signal; and
   computing a heart rate based on the detected peaks.

2. The method of claim 1, wherein rectifying the filtered demodulated Doppler ultrasound signal comprises applying one selected from a group consisting of an active full wave rectifier or an active half wave rectifier to the filtered demodulated Doppler ultrasound signal.

3. The method of claim 1, wherein the demodulated Doppler ultrasound signal is an in phase (I) component of the Doppler ultrasound signal.

4. The method of claim 1, wherein a passband of the second low-pass filter is set to a highest expected frequency for a heart rate.

5. The method of claim 4, wherein the highest expected frequency is 4 Hertz.

6. A heart rate monitoring system comprising:
   a bandpass filter adapted to:
      receive a demodulated Doppler ultrasound signal;
      filter the demodulated Doppler ultrasound signal to generate a filtered demodulated Doppler ultrasound signal;
   a signal-to-noise-ratio (SNR) estimator coupled to the bandpass filter, the SNR estimator comprising a first low-pass filter and adapted to:
      determine a peak in the filtered demodulated Doppler ultrasound signal;
      determine, using the first low-pass filter, an average of the filtered demodulated Doppler ultrasound signal; and
      estimate a SNR based on the peak and average of the filtered demodulated Doppler ultrasound signal;
   a frequency adapter coupled to the SNR estimator and adapted to modify a lower cutoff frequency of the bandpass filter based on the estimated SNR when the estimated SNR is below a pre-determined SNR threshold;

the modified bandpass filter further adapted to filter the filtered demodulated Doppler ultrasound signal to generate a double-filtered demodulated Doppler ultrasound signal;

a rectifier coupled to the frequency adapter and adapted to rectify the double-filtered demodulated Doppler ultrasound signal to generate a rectified filtered demodulated Doppler ultrasound signal;

a second low-pass filter coupled to the rectifier and adapted to filter the rectified filtered demodulated Doppler ultrasound signal to generate a resulting signal;

a microcontroller coupled to the second low-pass filter and adapted to:
  detect peaks in the resulting signal; and
  compute a heart rate based on the detected peaks.

7. The heart rate monitoring system of claim 6, wherein the rectifier is either an active full wave rectifier or an active half wave rectifier.

8. The heart rate monitoring system of claim 6, wherein the demodulated Doppler ultrasound signal is an in phase (I) component of the Doppler ultrasound signal.

9. The heart rate monitoring system of claim 6, wherein a passband of the second low-pass filter is set to a highest expected frequency for a heart rate.

10. The heart rate monitoring system of claim 9, wherein the highest expected frequency is 4 Hertz.

* * * * *